(12) United States Patent
Sweeney et al.

(10) Patent No.: US 10,232,186 B2
(45) Date of Patent: Mar. 19, 2019

(54) METHOD OF FORMING CONNECTOR BLOCKS FOR A HEADER OF AN IMPLANTABLE DEVICE

(71) Applicant: Cardiac Pacemakers, Inc., St. Paul, MN (US)

(72) Inventors: Moira B. Sweeney, St. Paul, MN (US); Michael J. Kane, Roseville, MN (US); James Fouhy, Co Cork (IE)

(73) Assignee: Cardiac Pacemakers, Inc., St. Paul, MN (US)

( * ) Notice: Subject to any disclaimer, the term of this patent is extended or adjusted under 35 U.S.C. 154(b) by 183 days.

(21) Appl. No.: 15/152,774

(22) Filed: May 12, 2016

(65) Prior Publication Data

US 2016/0250482 A1    Sep. 1, 2016

Related U.S. Application Data

(62) Division of application No. 14/190,405, filed on Feb. 26, 2014, now Pat. No. 9,345,894.

(60) Provisional application No. 61/773,302, filed on Mar. 6, 2013.

(51) Int. Cl.
| | |
|---|---|
| *H01R 13/33* | (2006.01) |
| *A61N 1/375* | (2006.01) |
| *H01R 43/20* | (2006.01) |
| *H01R 101/00* | (2006.01) |

(52) U.S. Cl.
CPC ........... *A61N 1/3752* (2013.01); *A61N 1/375* (2013.01); *H01R 13/33* (2013.01); *H01R 43/20* (2013.01); *H01R 2101/00* (2013.01); *Y10T 29/49826* (2015.01)

(58) Field of Classification Search
CPC ...... A61N 1/375; A61N 1/3752; H01R 43/20; H01R 13/33; H01R 2101/00; Y10T 29/49826

See application file for complete search history.

(56) References Cited

U.S. PATENT DOCUMENTS

| | | | |
|---|---|---|---|
| 3,074,046 A | 1/1963 | Sullivan | |
| 4,352,531 A * | 10/1982 | Gutter | H01R 12/775 439/497 |
| 4,655,462 A | 4/1987 | Balsells | |
| 4,838,815 A | 6/1989 | Tajima et al. | |

(Continued)

FOREIGN PATENT DOCUMENTS

| | | |
|---|---|---|
| CN | 101175528 A | 5/2008 |
| CN | 105025983 A | 11/2015 |

(Continued)

OTHER PUBLICATIONS

"U.S. Appl. No. 14/190,405, Corrected Notice of Allowance dated Dec. 31, 2015", 2 pgs.

(Continued)

*Primary Examiner* — Minh Trinh
(74) *Attorney, Agent, or Firm* — Schwegman Lundberg & Woessner P.A.

(57) ABSTRACT

A method includes placing a plastic connector block housing portion into a connector block cavity of a header; placing a coil spring into the connector block housing portion; and connecting a metallic termination member to the coil spring and positioning the metallic termination member to be exposed outside the plastic housing portion.

11 Claims, 5 Drawing Sheets

(56) References Cited

U.S. PATENT DOCUMENTS

| | | | |
|---|---|---|---|
| 4,848,346 | A | 7/1989 | Crawford |
| 5,012,807 | A | 5/1991 | Stutz, Jr. |
| 5,067,903 | A | 11/1991 | Szyszkowski |
| 5,076,270 | A | 12/1991 | Stutz, Jr. |
| 5,235,742 | A | 8/1993 | Szyszkowski |
| 5,282,841 | A | 2/1994 | Szyszkowski |
| 6,183,305 | B1 | 2/2001 | Doan et al. |
| 6,205,358 | B1 | 3/2001 | Haeg et al. |
| 6,835,084 | B2 | 12/2004 | Poon et al. |
| 6,862,478 | B1 | 3/2005 | Goldstein |
| 6,878,013 | B1 | 4/2005 | Behan |
| 7,083,474 | B1 | 8/2006 | Fleck et al. |
| 7,110,827 | B2 | 9/2006 | Sage et al. |
| 7,274,963 | B2 | 9/2007 | Spadgenske |
| 7,316,593 | B2 | 1/2008 | Balsells |
| 7,654,843 | B2 | 2/2010 | Olson et al. |
| 7,914,351 | B2 | 3/2011 | Balsells et al. |
| 8,500,499 | B2 | 8/2013 | Drew et al. |
| 8,735,751 | B2 | 5/2014 | Rust |
| 9,345,894 | B2 | 5/2016 | Sweeney et al. |
| 2005/0186829 | A1 | 8/2005 | Balsells |
| 2006/0047322 | A1 | 3/2006 | Naviaux |
| 2006/0161215 | A1 | 7/2006 | Naviaux |
| 2006/0224208 | A1 | 10/2006 | Naviaux |
| 2008/0214063 | A1 | 9/2008 | Hsiao et al. |
| 2008/0274651 | A1 | 11/2008 | Boyd et al. |
| 2012/0053663 | A1 | 3/2012 | Rodby et al. |
| 2012/0089203 | A1 | 4/2012 | Shaffer |
| 2012/0129409 | A1 | 5/2012 | Drew et al. |
| 2013/0096366 | A1 | 4/2013 | Bervoets et al. |
| 2014/0256184 | A1 | 9/2014 | Sweeney et al. |
| 2014/0336735 | A1 | 11/2014 | Kane et al. |
| 2016/0250482 | A1* | 9/2016 | Sweeney .............. A61N 1/375 29/874 |

FOREIGN PATENT DOCUMENTS

| | | |
|---|---|---|
| CN | 105025983 B | 4/2017 |
| JP | 2005518894 A | 6/2005 |
| JP | 2008534226 A | 8/2008 |
| JP | 2016508829 A | 3/2016 |
| WO | WO-2006107994 A1 | 10/2006 |
| WO | WO-2014137684 A2 | 9/2014 |
| WO | WO-2014137684 A3 | 9/2014 |
| WO | WO-2014186330 A1 | 11/2014 |

OTHER PUBLICATIONS

"U.S. Appl. No. 14/190,405, Final Office Action dated Jul. 22, 2015", 7 pgs.
"U.S. Appl. No. 14/190,405, Non Final Office Action dated Apr. 3, 2015", 9 pgs.
"U.S. Appl. No. 14/190,405, Notice of Allowance dated Jan. 29, 2016", 7 pgs.
"U.S. Appl. No. 14/190,405, Notice of Allowance dated Oct. 5, 2015", 7 pgs.
"U.S. Appl. No. 14/190,405, Response filed Jul. 2, 2015 to Non Final Office Action dated Apr. 3, 2015", 8 pgs.
"U.S. Appl. No. 14/190,405, Response filed Sep. 22, 2015 to Final Office Action dated Jul. 22, 2015", 7 pgs.
"U.S. Appl. No. 14/276,105, Non Final Office Action dated Nov. 23, 2015", 11 pgs.
"U.S. Appl. No. 14/276,105, Response filed Oct. 19, 2015 to Restriction Requirement dated Aug. 17, 2015", 7 pgs.
"U.S. Appl. No. 14/276,105, Restriction Requirement dated Aug. 17, 2015", 6 pgs.
"International Application Serial No. PCT/US2014/018542, International Preliminary Report on Patentability dated Sep. 17, 2015", 8 pgs.
"International Application Serial No. PCT/US2014/018542, International Search Report dated May 16, 2014", 4 pgs.
"International Application Serial No. PCT/US2014/018542, Written Opinion dated May 16, 2014", 6 pgs.
"International Application Serial No. PCT/US2014/037790, International Preliminary Report on Patentability dated Nov. 26, 2015", 8 pgs.
"International Application Serial No. PCT/US2014/037790, International Search Report dated Sep. 24, 2014", 4 pgs.
"International Application Serial No. PCT/US2014/037790, Written Opinion dated Sep. 24, 2014", 6 pgs.
"U.S. Appl. No. 14/276,105, Advisory Action dated Sep. 6, 2016", 3 pgs.
"U.S. Appl. No. 14/276,105, Final Office Action dated Jun. 6, 2016", 10 pgs.
"U.S. Appl. No. 14/276,105, Final Office Action dated Oct. 19, 2017", 10 pgs.
"U.S. Appl. No. 14/276,105, Non Final Office Action dated Mar. 9, 2018", 10 pgs.
"U.S. Appl. No. 14/276,105, Non Final Office Action dated Apr. 3, 2017", 9 pgs.
"U.S. Appl. No. 14/276,105, Response filed Jan. 18, 2018 to Final Office Action dated Oct. 19, 2017", 9 pgs.
"U.S. Appl. No. 14/276,105, Response filed Jun. 29, 2017 to Non Final Office Action dated Apr. 3, 2017", 8 pgs.
"U.S. Appl. No. 14/276,105, Response filed Aug. 8, 2016 to Final Office Action dated Jun. 6, 2016", 7 pgs.
"U.S. Appl. No. 14/276,105, Response to Non Final Office Action dated Nov. 23, 2015", 10 pgs.
"Chinese Application Serial No. 201480012223.8, Office Action dated Mar. 29, 2016", W/ English Translation, 19 pgs.
"Chinese Application Serial No. 201480012223.8, Office Action dated Sep. 28, 2016", W/ English Translation, 9 pgs.
"Chinese Application Serial No. 201480012223.8, Response filed Aug. 9, 2016 to Office Action dated Mar. 29, 2016", w/ Claims in English, 12 pgs.
"Chinese Application Serial No. 201480012223.8, Response filed Dec. 13, 2016 to Office Action dated Sep. 28, 2016", W/ English Claims.
"Japanese Application Serial No. 2015-561394, Office Action dated Jul. 19, 2016", With English Translation, 3 pgs.
"Japanese Application Serial No. 2015-561394, Response filed Dec. 14, 2016 to Office Action dated Jul. 19, 2016", w/ Claims in English.

\* cited by examiner

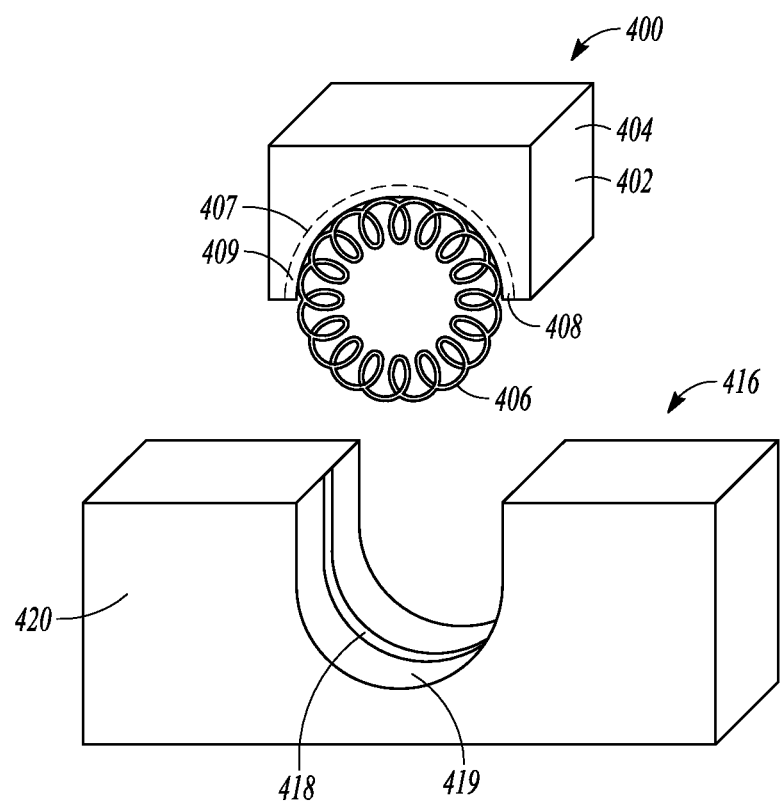
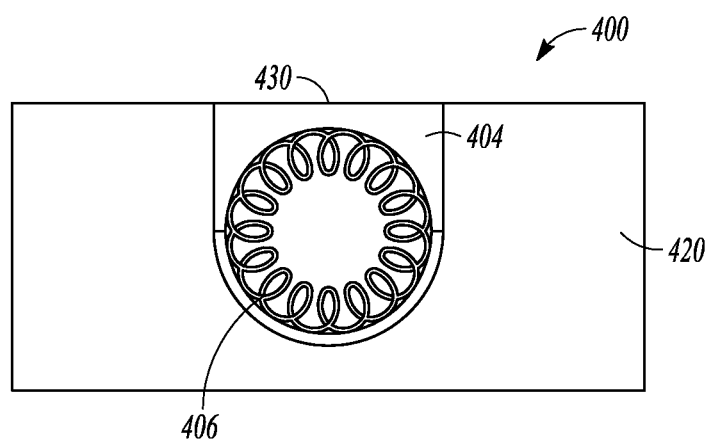
FIG. 10

METHOD OF FORMING CONNECTOR BLOCKS FOR A HEADER OF AN IMPLANTABLE DEVICE

CLAIM OF PRIORITY

This application is a division of U.S. application Ser. No. 14/190,405, filed Feb. 26, 2014, which claims the benefit of priority under 35 U.S.C. § 119(e) of U.S. Provisional Patent Application Ser. No. 61/773,302, filed on Mar. 6, 2013, each of which is herein incorporated by reference in its entirety.

BACKGROUND

Implantable devices such as pacemakers or defibrillators include a housing and an attached header. The header includes one or more ports to receive a terminal end of an implantable lead. The header includes connector blocks with contacts that electrically communicate with terminal contacts on the lead. The connector block contacts are electrically connected to feedthroughs which contact electronics within the housing. U.S. Pat. No. 5,076,270 discusses header contacts for an implantable device.

OVERVIEW

Example 1 can include subject matter that can include an apparatus comprising: an implantable housing; a header mounted to the implantable housing and including a connector block cavity; and a connector block located within the connector block cavity, the connector block including a plastic housing portion, a coil spring, and a metallic termination member connected to the coil spring and exposed outside the plastic housing portion.

In Example 2, the subject matter of claim 1 can optionally include the metallic termination member being non-circumferential around the coil spring.

In Example 3, the subject matter of any of Examples 1 or 2 can optionally include the connector block cavity being open on a side of the header such that the connector block is side-mounted into the header.

In Example 4, the subject matter of any of Examples 1-3 can optionally include the plastic housing portion including a receiver section configured to receive at least a portion of the coil spring.

In Example 5, the subject matter of any of Examples 1-4 can optionally include the plastic housing portion being integral to the header within the connector block cavity.

In Example 6, the subject matter of any of Examples 1-4 can optionally include the plastic housing portion including a discrete plastic housing body mounted within the connector block cavity.

In Example 7, the subject matter of any of Examples 1-4 or 6 can optionally include the metallic termination member including a flat ribbon connector.

In Example 8, the subject matter of any of Examples 1-6 can optionally include the metallic termination member including a metallic block including at least a portion configured to receive the canted coil spring.

In Example 9, the subject matter of any of Examples 1-4 or 6-8 can optionally include the plastic housing portion including a flat, planar outer surface with the flat connector ribbon lying flush against the flat, planar outer surface.

In Example 10, the subject matter of any of Examples 1-4 or 6-8 can optionally include the plastic housing portion including a non-planar outer surface.

In Example 11, the subject matter of any of Examples 1-4 or 6-8 can optionally include the metallic termination member including a flat ribbon connector which extends away from the connector block and connected directly to a feedthrough.

In Example 12, the subject matter of any of Examples 1-11 can optionally include the header including a header core overmolded with an epoxy.

Example 13 can include subject matter that can include an apparatus comprising: an implantable housing; a header mounted to the implantable housing and including a plastic header core having a connector block cavity; and a connector block located within the connector block cavity, the connector block including a plastic housing portion holding a spring and a metallic termination member connected to the spring and exposed outside the plastic housing portion; wherein the header core is overmolded with an epoxy to encapsulate the connector block and the header core.

In Example 14, the subject matter of Example 13 can optionally include the metallic termination member being non-circumferential around the spring.

In Example 15, the subject matter of any of Examples 13-14 can optionally include the plastic housing portion including a receiver section configured to receive at least a portion of the spring.

In Example 16, the subject matter of any of Examples 13-15 can optionally include the plastic housing portion being integral to the header within the connector block cavity.

In Example 17, the subject matter of any of Examples 15 can optionally include the plastic housing portion including a discrete plastic housing body mounted within the connector block cavity.

Example 18 can include subject matter that can include a method comprising: placing a plastic connector block housing portion into a connector block cavity of a header; placing a coil spring into the connector block housing portion; and connecting a metallic termination member to the coil spring and positioning the metallic termination member to be exposed outside the plastic housing portion.

In Example 19, the subject matter of Example 18 can optionally include the metallic termination member being non-circumferential around the coil spring.

In Example 20, the subject matter of any of Examples 18 or 19 can optionally include overmolding the header with an epoxy.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9 shows an exploded perspective view of a connector block, in accordance with one example.

FIG. 10 shows a side view of the connector block of FIG. 9.

DETAILED DESCRIPTION

Figure 1:
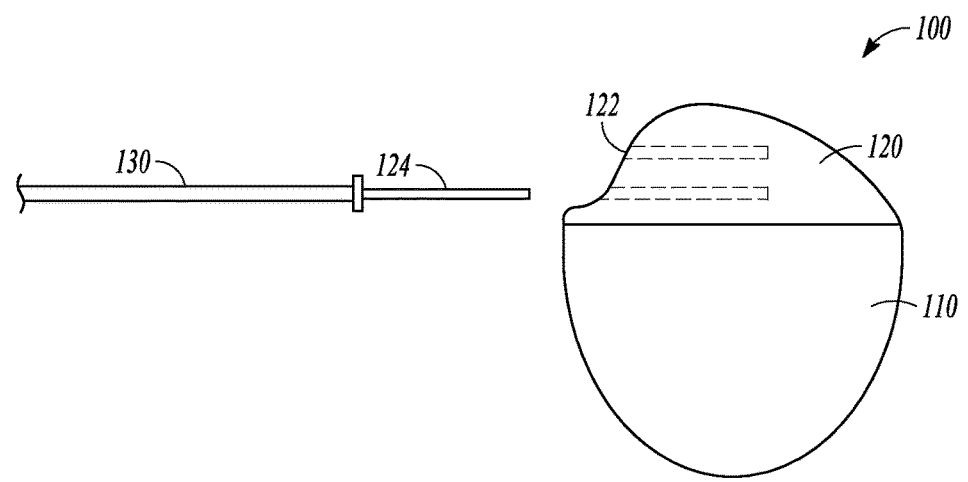
FIG. 1 shows an implantable medical device in accordance with one example.

FIG. 1 shows an implantable medical device 100 in accordance with one example. The implantable medical device 100 includes a metallic housing 110 and an attached header 120. The header 120 includes one or more ports 122 to receive a terminal pin 124 of an implantable lead 130. The lead 130 is configured to deliver pacing pulses, defibrillation shock energy, or cardioversion therapy to a heart, for example. The implantable medical device 100 can be implanted in a surgically-formed pocket in a patient's chest or other desired location. The implantable medical device 100 generally includes electronic components to perform signal analysis, processing, and control. The implantable medical device 100 can include a power supply such as a battery, a capacitor, and other components housed within housing 110. The implantable medical device 100 can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia via one or more electrodes of the lead 130.

Figure 2:
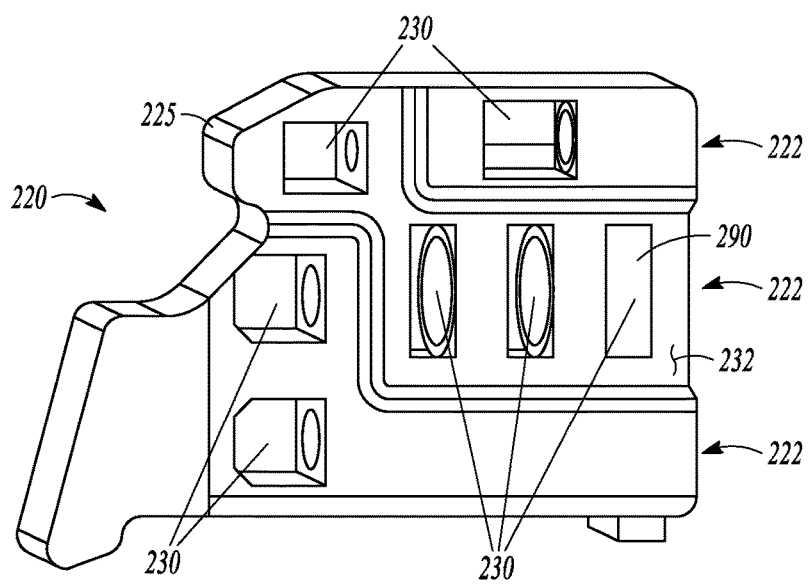
FIG. 2 shows a perspective view of a header core for a header of an implantable medical device, in accordance with one example.

FIG. 2 shows a perspective view of a header core 220 for a header of an implantable medical device, in accordance with one example. The header core 220 can include a core body 225, formed of molded plastic, for example. The header core 220 can include one or bores 222 formed in the header core body 225 to receive a terminal pin of a lead. The header core 220 can include one or more connector block cavities 230. The connector block cavities 230 can be open on a side surface 232 of the header core 220. The connector block cavities 230 can be shaped and dimensioned to each receive a connector block 290. The connector block 290 can be side-mounted into the side surface located connector block cavities 230 of the header core 220. The connector block 290 can be connected to feedthroughs that extend from the header into a housing of an implantable device. Thus, the connector block 290 can receive a lead terminal pin and electrically couple the lead terminal pin to electronics within the housing via the feedthrough.

Figure 3:
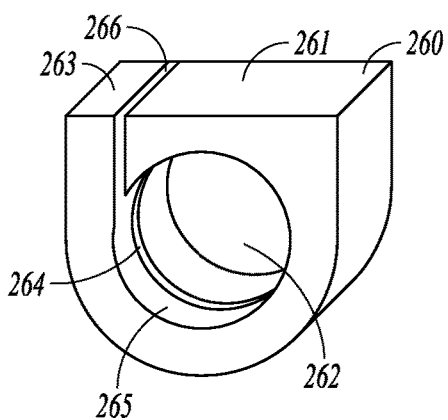
FIG. 3 shows a perspective view of a connector block housing in accordance with one example.
Figure 4:
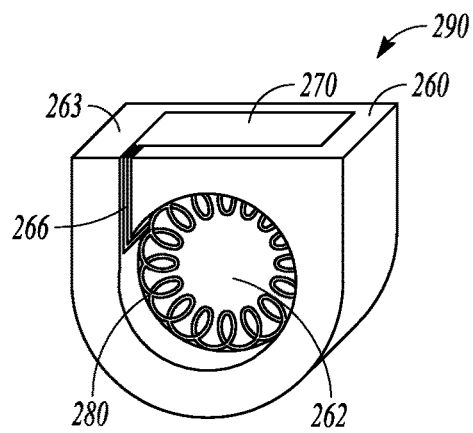
FIG. 4 shows a perspective view of a connector block in accordance with one example.

FIG. 3 shows a perspective view of a connector block plastic housing portion 260 in accordance with one example; and FIG. 4 shows a perspective view of the connector block 290 in accordance with one example.

The plastic housing portion 260 can include a discrete molded plastic body 261 which is dimensioned to at least partially fit within the connector block cavity 230 (FIG. 2). The plastic housing portion 260 can include a bore 262 configured to receive a spring, such as a canted coil spring 280, therein. The plastic housing portion 260 can include a coil spring receiving section 264, such as a race or groove 265 formed in the surface of the plastic housing portion 260 around the periphery of the bore 262. In other options, walls or other structures can be formed in the bore 262 to receive and hold the coil spring 280.

The plastic housing portion 260 can include a slot 266 which extends from the bore 262 to an exterior of the plastic housing portion 260. The slot 266 can hold a metallic termination member 270 which extends from the coil spring 262 to an exterior of the plastic housing portion 260. The metallic termination member 270 can be formed of stainless steel, MP35N, or other suitable metallic materials. The metallic termination member 270 can be connected to the coil spring 280, extend through the slot 266 and be formed to lie flush on an exposed outer surface 263 of the plastic housing portion 260. Plastic housing portion 260 can include a flat, planar, outer surface 263. The flat, planar outer surface 263 provides for ease of further connections to the metallic termination member 270.

Figure 5:
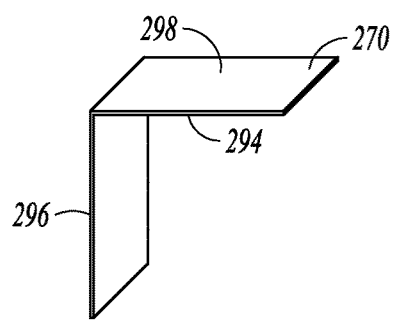
FIG. 5 shows a perspective view of a termination member, in accordance with one example.

FIG. 5 shows a perspective view of the metallic termination member 270, in accordance with one example. The metallic termination member 270 can include a flat ribbon connector 294 formed by stamping, for example. The metallic termination member can include an L-shape with a first end 296 to attach to the coil spring and an upper surface 298 for attachment of the connector 294 to a feedthrough.

Figure 6:
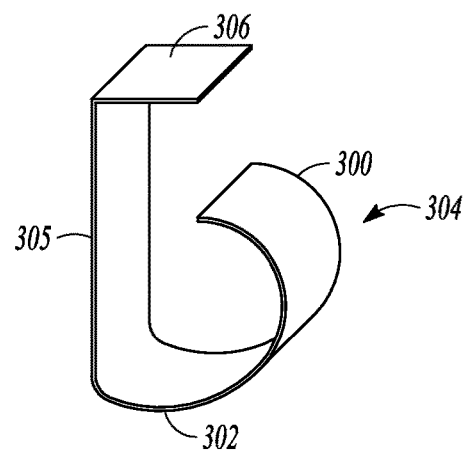
FIG. 6 shows a perspective view of a termination member, in accordance with one example.

FIG. 6 shows a perspective view of a metallic termination member 300, in accordance with one example. The metallic termination member 300 can include a flat ribbon connector 302 formed by stamping, for example. The metallic termination member 300 can include a curled portion 304 dimensioned to partially enclose the coil spring 280. The metallic termination member 300 can include a straight lead-out section 305 and a flat upper connection surface 306. The metallic termination member 300 can be mounted within the connector block plastic housing portion 260 (FIG. 3) such that the curled portion 304 is within the bore 262, the lead-out section 305 extends through the slot 266 and the upper connections surface 306 lies flush against the outer surface 263 of the plastic housing portion 260. The coiled spring 280 is then mounted within the curled portion 304.

For each of the metallic termination members 270 and 300 discussed above, the metallic termination members 270 and 300 can be non-circumferential or hemi-circular around the coil spring 280. This allows for ease of manufacture and lower costs. Past block connectors included a canted coil spring mounted within a metallic housing having a race to circumferentially hold the spring. Forming such a circumferential metallic housing requires the metallic housing to be machined. In contrast, the plastic housing portion 260 of connector block 290 can be formed of molded plastic and the metallic termination members 270, 300 can be formed by metal stamping. These are relatively cheaper processes and use lower cost materials than machining a completely circumferential metallic part.

Figure 7A:
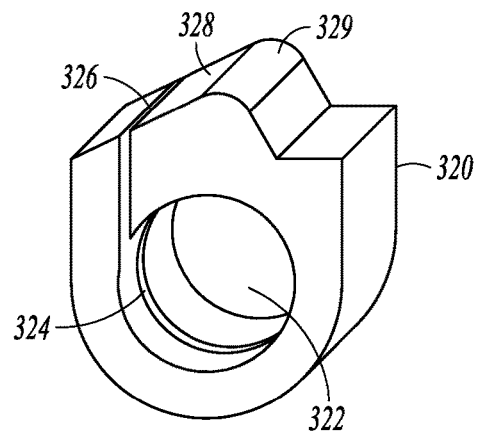
FIG. 7A shows a perspective view of a connector block housing in accordance with one example.

FIG. 7A shows a perspective view of a connector block plastic housing portion 320 in accordance with one example. The plastic housing portion 320 can include a molded plastic body and includes a bore 322, a coil spring receiving section 324, and a slot 326 configured to receive the coil spring 280 and the metallic termination member 270, 300. The plastic housing portion 320 can include a non-planar outer surface 328. Non-planar outer surface 328 can include a ramped portion 329 or other shape configured to provide an easier connection surface for attaching a connector to the metallic termination member depending on the electronic configuration or feedthrough position of the implantable device.

Figure 7B:
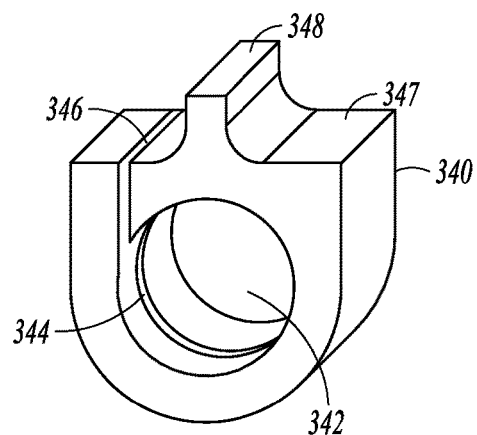
FIG. 7B shows a perspective view of a connector block housing in accordance with one example.

FIG. 7B shows a perspective view of a connector block plastic housing portion 340 in accordance with one example. The plastic housing portion 340 can include a molded plastic body and includes a bore 342, a coil spring receiving section 344, and a slot 346 configured to receive the coil spring 280 and the metallic termination member 270, 300 (FIG. 4). The plastic housing portion 340 can include a non-planar outer surface 347. The non-planar outer surface 347 can include a projection 348. The projection 348 can provide electrical insulation for the metallic termination member 270, 300 from wires running on the other side of the projection 348.

Figure 8A:
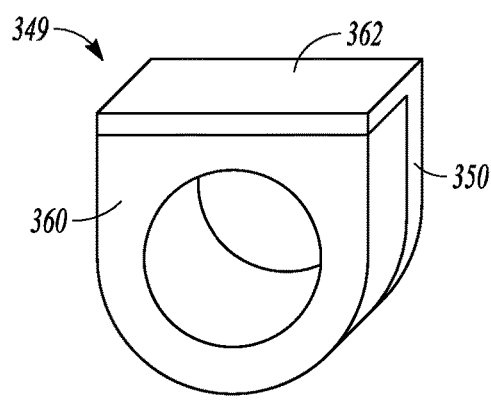
FIG. 8A shows a perspective view of a connector block in accordance with one example.
Figure 8B:
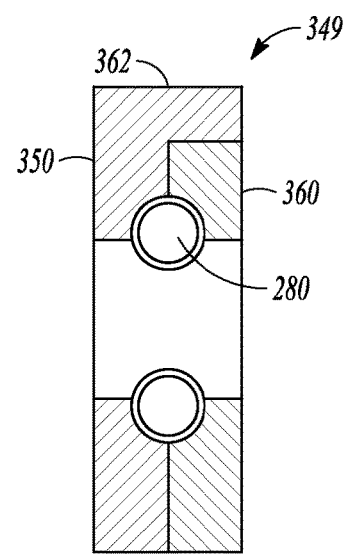
FIG. 8B shows a side cross-section view of the connector block of FIG. 8A.

FIG. 8A shows a perspective view of a connector block 349 in accordance with one example; and FIG. 8B shows a side cross-section view of the connector block 349. The connector block 349 includes a partially nested structure with a plastic housing portion 360 which is dimensioned to fit with a metallic termination member 350, both of which hold the coil spring 280. The metallic termination member 350 can be formed of stainless steel, MP35N, or other suitable metallic materials. The metallic termination member 350 includes an upper surface 362 for attachment of connector to a feedthrough.

FIG. 9 shows an exploded perspective view of a connector block 400, in accordance with one example; and FIG. 10 shows a side view of the connector block 400.

The connector block 400 can include a metallic termination member 402, such as a metallic block 404. Metallic block 404 can include a partial block such that the metallic block 404 does not encircle a canted coil spring 406. The metallic block 404 can be a half-block, a ¾-block, or a ¼-block for example. The metallic block 404 can be formed by molding from stainless steel, MP35N, or other suitable metallic material. By forming the metallic block 404 as non-circumferential around coil spring 406, the metallic block 404 can be molded or sintered instead of machined, as required by circumferential connector blocks. The metallic block 404 can include an arched portion 407 including a coil spring receiving section 408. The coil spring receiving area 408 can include a groove 409.

The connector block 400 can further include a connector block plastic housing portion 416 including a coil spring receiving section 418 formed integral with a plastic header core 420. The coil receiving section 418 can include a groove 419. Thus, the plastic housing portion 416 can be integrally formed as part of a connector block cavity of the header core 420 when the plastic header core 420 is molded. The plastic housing portion 416 can matingly receive the coil spring 408 and the metallic block 404. The coil spring receiving section 408 of the metallic block 404 and the coil spring receiving section 418 of the plastic housing portion 416 can be aligned to form a circumferential receiving section for the coil spring 406. In an example, the metallic block groove 409 can be aligned with the plastic housing portion grove 419 to define a circumferential groove to receive the coil spring 406. The metallic block 404 can be mounted within the plastic housing portion 416 and attached to the header core 420. A connector attachment can be made at an upper attachment surface 430 of the metallic block 404.

Figure 11:
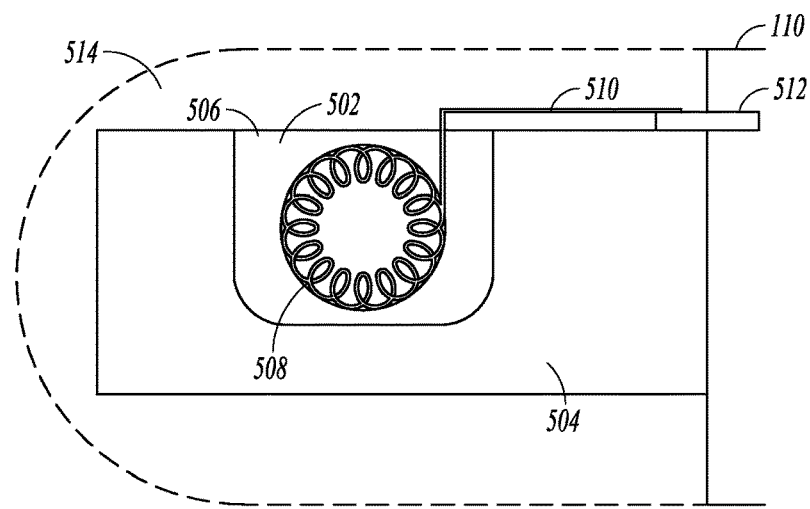
FIG. 11 shows a side view of a connector block connection to a feedthrough, in accordance with one example.

FIG. 11 shows a side view of a connector block 502 connection to a feedthrough 512, in accordance with one example. The connector block 502 can include a connector block plastic housing 506 and a coil spring 508, such as discussed above. A metallic termination member 510 can include a flat ribbon connector and can be connected to the coil spring 508 and can extend to connect directly to the feedthrough 512 which communicates internally to housing 110. This structure eliminates having to weld a connector between the metallic termination member and the feedthrough 512. The single weld thus can reduce complexity and increase reliability compared to a two weld connection. An overmold 514 encapsulates the header core in this example. In some embodiments, a pre-molded header can be utilized and the connector blocks can be covered by a medical adhesive sealant.

Figure 12:
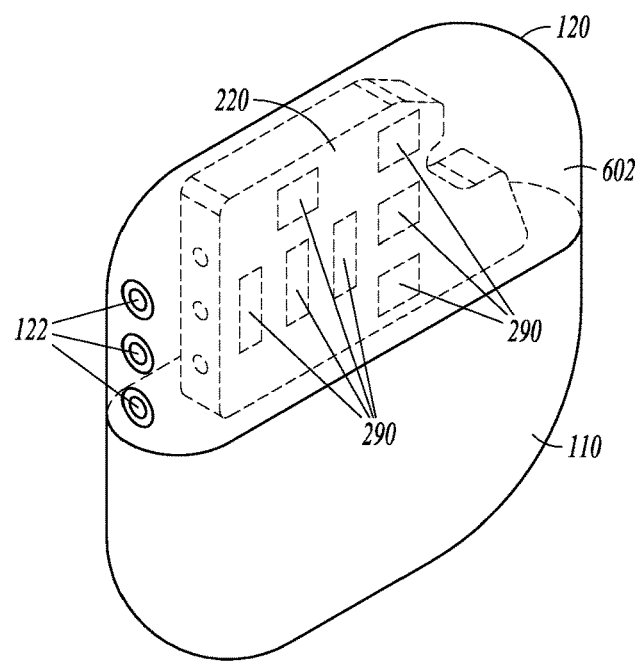
FIG. 12 shows a perspective view of an implantable medical device, in accordance with one example.

FIG. 12 shows a perspective view of the implantable medical device 100, in accordance with one example. The implantable medical device 100 can include the header 120 mounted to the housing 110. The header 120 can include the header core 220 with the connector blocks 290 mounted into the connector block cavities of the header core 220. The connector blocks 290 can be formed as discussed above and side-loaded into the header core 220. In forming a header with the connector block discussed herein, one example can include placing a plastic connector block housing portion into a connector block cavity of a header, placing a coil spring into the connector block housing portion, and connecting a metallic termination member to the coil spring and positioning the metallic termination member to be exposed outside the plastic housing portion. After all the connections have been made between the connector blocks 290 and the feedthroughs of the housing 110, the header core 220 can be encapsulated with an epoxy overmold 602.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. A method comprising:
providing a plastic connector block housing portion;
placing the plastic connector block housing portion into a connector block cavity of a header;
providing a coil spring;
placing the coil spring into the connector block housing portion;
providing a metallic termination member; and
connecting the metallic termination member to the coil spring and positioning the metallic termination member to be exposed outside the plastic housing portion such that the plastic housing portion includes a planar outer surface with the metallic termination member lying flush against the planar outer surface.

2. The method of claim 1, wherein connecting the metallic termination member to the coil spring includes positioning the metallic termination member to be non-circumferential around the coil spring.

3. The method of claim 1, further including overmolding the header with an epoxy.

4. The method of claim 1, further including coupling the metallic termination member to a feedthrough that extends from a housing to the header.

5. The method of claim 1, wherein placing the plastic connector block housing portion includes placing the connector block housing portion into the connector block cavity on an open side of the header such that the connector block is side-mounted into the header.

6. The method of claim 1, wherein placing the coil spring includes the plastic housing portion including a receiver section configured to receive at least a portion of the coil spring.

7. The method of claim 1, wherein placing the plastic connector block housing portion includes the plastic housing portion being integral to the header within the connector block cavity.

8. The method of claim 1, wherein placing the plastic connector block housing portion includes the plastic housing portion being a discrete plastic housing body mounted within the connector block cavity.

9. The method of claim 1, wherein providing a metallic termination member includes providing a flat ribbon connector.

10. The method of claim 1, wherein providing a metallic termination member includes providing a metallic block including at least a portion configured to receive the coil spring.

11. The method of claim 1, wherein providing a metallic termination member includes providing a metallic termination member that includes a flat ribbon connector which extends away from the connector block and is connected directly to a feedthrough.

* * * * *